United States Patent [19]

Haacke

[11] Patent Number: 4,579,127
[45] Date of Patent: Apr. 1, 1986

[54] MANDREL FOR HOSE TYPE CATHETERS AND BODY PROBES

[75] Inventor: Claus Haacke, Melsungen, Fed. Rep. of Germany

[73] Assignee: Intermedicat GmbH, Emmenbrucke, Switzerland

[21] Appl. No.: 635,231

[22] Filed: Jul. 27, 1984

[30] Foreign Application Priority Data

Aug. 2, 1983 [DE] Fed. Rep. of Germany ....... 3327779

[51] Int. Cl.$^4$ ............................................. A61M 25/00
[52] U.S. Cl. ..................................... 128/772; 604/170
[58] Field of Search ....................... 604/170, 164, 280; 128/656–658, 772

[56] References Cited

U.S. PATENT DOCUMENTS

| 3,612,058 | 10/1971 | Ackerman | 604/170 X |
| 3,973,556 | 8/1976 | Fleischhacker | 128/772 |
| 4,257,421 | 3/1981 | Beal | 128/772 X |
| 4,362,163 | 12/1982 | Krick | 604/280 |
| 4,504,268 | 3/1985 | Herlitze | 604/170 |

Primary Examiner—Dalton L. Truluck
Attorney, Agent, or Firm—Kenyon & Kenyon

[57] ABSTRACT

A mandrel for use with a catheter or body probe comprises at least four outer wires which are spirally wound with a high pitch around a straight wire core. The outer wires are covered by a coating of plastic of uniform thickness wherein the coating is sufficiently thin so that the contours of the outer wires are preserved on the outer side of the mandrel. Each turn of the outer wires has a large component in longitudinal direction, and the mandrel is easily displaceable within the catheter.

16 Claims, 4 Drawing Figures

MANDREL FOR HOSE TYPE CATHETERS AND BODY PROBES

FIELD OF THE INVENTION

This invention relates to a mandrel for hose type catheters or body probes comprising a wire core helically wrapped with an outer wire.

BACKGROUND OF THE INVENTION

Catheters and body probes which are introduced into human body cavities must be soft so as not to cause injuries to the patient. For introducing a catheter or a body probe into the body in a controlled manner, e.g., into a blood vessel, the bladder, the stomach or the intestine, a stiffening element must be introduced into the interior of the hose, so that the hose will be sufficiently stiff during the insertion. Such a stiffening element is referred to as a mandrel.

Often it is customary to first introduce the stiffening element into the body and then to slip the hose over it. Thereafter, the thin mandrel, also referred to as a Seldinger wire, is extracted from the hose.

A known mandrel (Zeitschrift Anaesthesist, 29, 498 to 503) comprises a wire core which is surrounded by a helically or spirally wound single outer wire. The wire core forms a safety wire and governs the stiffness of the mandrel, whereas the outer wire is much thinner and very flexible. The turns of the outer wire are also close together, so that the pitch of the outer wire is 1:1, that is, the distance between the center axes of adjacent turn equals the thickness of the outer wire. Thus, the outer wire is almost transverse to the lengthwise direction of the mandrel. When the mandrel is inserted into a narrow hose, relatively great friction results between the numerous turns of the outer wire and the inside wall of the hose.

It is further known how to embed a guide wire either as single wire or as braid into a thick-walled plastic jacket (EP-PS 0,014,424, DE-GM 81 23 912, DE-GM 81 32 829). The plastic jacket has a cylindrical outer surface whereby the outer surface of the mandrel contacts the entire area of the inner wall of a thin hose. This results in a large-area contact between the mandrel and hose, so that it is often difficult to move the mandrel and hose relative to each other because the friction is great. Even when using especially well-sliding materials, such as FEP or PTFE, the adhesion of the two parts is difficult to overcome because of the surface adhesion of the two smooth polymer surfaces and as a result of curves which the hose assumes in the human body. It is, therefore, very difficult to pull the mandrel out of a narrow hose. The poor displaceability of the mandrel in the hose also leads to an increased assembly time in the manufacturer's plant. As a rule, the hoses are delivered with the mandrel inserted.

OBJECTS OF THE INVENTION

It is therefore an object of the present invention to provide a mandrel which is easy to displace in a narrow catheter, body probe or in another hose.

These and other objects of the present invention will become apparent from the following description and claims in conjunction with the drawings.

SUMMARY OF THE INVENTION

In accordance with the present invention, there is provided a mandrel comprising a wire core with at least four outer wires which are wound around the core with a high pitch of at least 5:1.

In the mandrel in accordance with the present invention, several outer wires are wrapped around the wire core in the manner of a cabling. The outer wires cover the total circumference of the wire core but have a relatively high pitch. By pitch is understood the ratio of the height of one turn to the thickness, e.g., diameter, of the outer wire. As a result of the high pitch, the outer wires extend with a considerable component in lengthwise direction of the mandrel, that is, in the pushing direction. That is, each turn of the outer wires has a large component in the longitudinal direction of the wire core. The contours of the outer wires stand out at a circumference of the mandrel. This means that the mandrel does not have a cylindrical outer surface. Rather, the surface of the mandrel is formed by the outer sides of the individual outer wires. A helical furrow extends between pairs of outer wires. Due to this formation of the surface of the mandrel, the surface adhesion of the mandrel to the hose into which the mandrel is inserted is considerably reduced. Only slight friction and adhesion resistance results between mandrel and hose because the outer wires have a high pitch and are oriented with each turn having a large component in lengthwise direction of the mandrel.

An essential advantage of the invention results from the fact that the number and diameter of the outer wires, as well as the diameter of the wire core, can be mutually matched in numerous variations. Therefore, a mandrel can be obtained with a stiffness favorable for the respective application. The total diameter of the mandrel and also the lateral flexibility thereof can be readily regulated by suitable selection of the wire core and of the outer wires.

There are preferably five to eight outer wires. The greater the number of the outer wires, the thicker may be the wire core. The thickness of the wire core determines the stiffness of the mandrel. If a mandrel of lesser stiffness is desired to be obtained, one chooses a thinner wire core and a smaller number of outer wires.

The pitch of the outer wires is preferably at least 7:1, but it may be substantially greater, e.g. 12:1 or greater.

According to an advantageous embodiment of the invention, the outer sides of the outer wires are coated with a plastic in the form of a film which is sufficiently thin so that the contours of the outer wires are preserved on the surface. The plastic film is thin and as uniform as possible, so that the wire structure stands out plastically on the surface of the mandrel. That is, the furrows between the outer wires are not filled with the plastic, so that the outer contour of the wire is distinguished from the cylindrical inner contour of the hose of the catheter or body probe. This thin plastic film prevents entrance of body fluid into the interior of the mandrel.

The wire core need not extend over the total length of the mandrel. Rather, it can end before the patient-side end of the mandrel, so that this end section has an increased flexibility compared with the remaining length of the mandrel. The end section may also be bent in J-form or tensioned.

DETAILED DESCRIPTION

Figure 1:
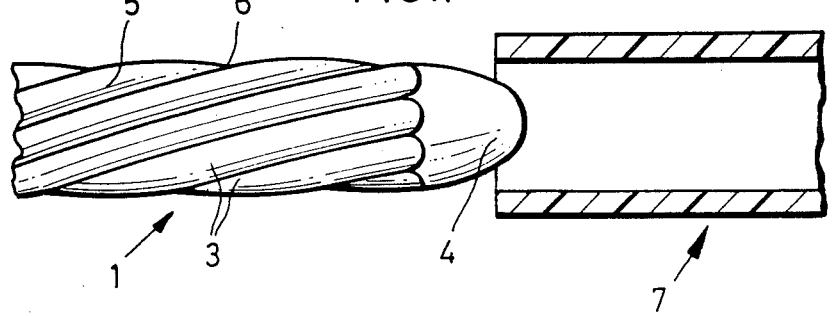
FIG. 1 schematically illustrates a side view of the patient-side end of a mandrel in accordance with the present invention with a sectional view of the end of a catheter.
Figure 2:
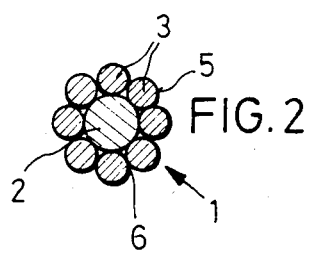
FIGS. 2 to 4 illustrate cross-sectional views of various embodiments of the mandrel in accordance with the present invention.

The mandrel 1 shown in FIG. 1, the cross-section of which is illustrated in FIG. 2, comprises a wire core 2 formed from an elongated straight wire of round cross-section. Seven outer wires 3 are arranged around the wire core 2. The outer wires 3 are wrapped helically around the wire core 2 with the pitch of each outer wire 3 being about 12:1. The outer wires 3 all have the same diameter. These diameters are smaller than the diameter of the wire core 2. At the patient-side end of the mandrel 1, the outer wires 3 are brought together in a plug 4 and are welded or soldered together. At its end, the plug 4 has the form of a rounded dome. The plug 4 may be fabricated from plastic or metal.

On the circumferential surface of the mandrel 1, on which stands out the approximately semi-circular outer sides of the outer wires 3, the mandrel 1 is provided with a plastic coating 5 of substantially uniform thickness. As can be seen from FIG. 2, the outer contour of the coating 5 follows the contour of the outer wires 3, and the coating is sufficiently thin so that there is a spiral furrow 6 between adjacent pairs of outer wires 3.

The mandrel is is inserted into the hose type catheter 7 according to FIG. 1. The catheter lumen (the inside diameter) substantially matches the outside diameter of mandrel 1. The mandrel 1 slides in the catheter 7 without any great adhesion resistance because the mandrel 1 abuts against the inner wall of catheter 7 only by the arches of the coating 5.

Figure 3:
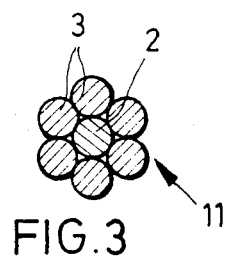

In the embodiment of the present invention illustrated in FIG. 2, the mandrel 1 is relatively stiff because the wire core 2 has a larger cross-section than the outer wires 3. If the mandrel is desired to have greater flexibility, one chooses the embodiment of the invention according to FIG. 3, wherein the wire core 2 has the same diameter as the outer wires 3. In the mandrel 11 illustrated in FIG. 3, six outer wires are evenly arranged around the circumference of the wire core 2.

Figure 4:
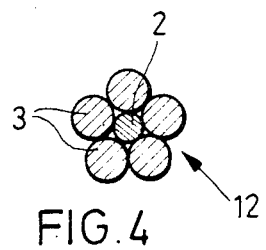

The mandrel 12 illustrated in FIG. 4 has a still greater flexibility. Mandrel 12 of FIG. 4 has five outer wires 3 arranged evenly around the wire core 2. The diameter of the wire core 2 is smaller than the diameter of outer wires 3.

In all embodiments, the outer wires 3 are in direct contact with the wire core 2. The outer wires are wrapped spirally around the wire core 2 in the manner of a cabling. A special advantage of the mandrel of the present invention is that it is simple to manufacture using known cabling techniques.

Although preferred embodiments of the present invention have been described in detail, it is contemplated that modifications may be made all in accordance with the spirit and scope of the present invention.

What is claimed is:

1. In a mandrel for hose type catheters or body probes having an elongated wire core wrapped with outer wire, the improvement comprising: at least four outer wires wound with a high pitch of at least 5:1 around the wire core wherein adjacent outer wires continuously abut one another and said outer wires cover the entire circumference of said wire core along the length of said wire core.

2. A mandrel according to claim 1 having 5 to 8 outer wires.

3. A mandrel according to claim 1 wherein the pitch of the outer wires is at least 7:1.

4. A mandrel according to claim 2 wherein the pitch of the outer wires is at least 7:1.

5. A mandrel according to claim 1 wherein the outer sides of the outer wires are coated with a plastic coating wherein the plastic coating is sufficiently thin so that the contours of the outer wires are preserved at the outer surface of the mandrel.

6. A mandrel according to claim 2 wherein the outer sides of the outer wires are coated with a plastic coating wherein the plastic coating is sufficiently thin so that the contours of the outer wires are preserved at the outer surface of the mandrel.

7. A mandrel according to claim 3 wherein the outer sides of the outer wires are coated with a plastic coating wherein the plastic coating is sufficiently thin so that the contours of the outer wires are preserved at the outer surface of the mandrel.

8. A mandrel according to claim 4 wherein the outer sides of the outer wires are coated with a plastic coating wherein the plastic coating is sufficiently thin so that the contours of the outer wires are preserved at the outer surface of the mandrel.

9. A mandrel according to claim 1 wherein at least at one end of the mandrel, the ends of the outer wires are enclosed by a plug fabricated from a material selected from the group consisting of plastic and metal.

10. A mandrel according to claim 2 wherein at least at one end of the mandrel, the ends of the outer wires are enclosed by a plug fabricated from a material selected from the group consisting of plastic and metal.

11. A mandrel according to claim 3 wherein at least at one end of the mandrel, the ends of the outer wires are enclosed by a plug fabricated from a material selected from the group consisting of plastic and metal.

12. A mandrel according to claim 4 wherein at least at one end of the mandrel, the ends of the outer wires are enclosed by a plug fabricated from a material selected from the group consisting of plastic and metal.

13. A mandrel according to claim 5 wherein at least at one end of the mandrel, the ends of the outer wires are enclosed by a plug fabricated from a material selected from the group consisting of plastic and metal.

14. A mandrel according to claim 6 wherein at least at one end of the mandrel, the ends of the outer wires are enclosed by a plug fabricated from a material selected from the group consisting of plastic and metal.

15. A mandrel according to claim 7 wherein at least at one end of the mandrel, the ends of the outer wires are enclosed by a plug fabricated from a material selected from the group consisting of plastic and metal.

16. A mandrel according to claim 8 wherein at least at one end of the mandrel, the ends of the outer wires are enclosed by a plug fabricated from a materal selected from the group consisting of plastic and metal.

* * * * *